US00PP36818P3

(12) United States Plant Patent
Olesen

(10) Patent No.: US PP36,818 P3
(45) Date of Patent: Jul. 15, 2025

(54) ROSE PLANT NAMED 'Poulty048'

(50) Latin Name: *Rosa hybrida*
Varietal Denomination: Poulty048

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,180

(22) Filed: Sep. 5, 2024

(65) Prior Publication Data

US 2025/0107465 P1 Mar. 27, 2025

(30) Foreign Application Priority Data

Sep. 22, 2023 (QZ) ..... PBR 20231982

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./122
CPC ..... A01H 5/0222
See application file for complete search history.

*Primary Examiner* — Kent L Bell

(57) ABSTRACT

A new garden rose plant of the Miniature class which has abundant, red flowers and attractive foliage. This new and distinct variety has shown to be uniform and stable in the resulting generations from asexual propagation.

2 Drawing Sheets

Botanical designation: *Rosa hybrida.*

Variety denomination: 'Poulty048'.

This application claims priority to Plant Breeder's Rights Application Number 2023/1982, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2019 and the resulting seeds were planted in a controlled environment in Fredensborg, Denmark. The new variety, named 'Poulty048', originated as a single seedling from the stated cross.

The new variety may be distinguished from its male pollen parent and female seed parent primarily by the following characteristics. The male pollen parent plant has red-purple flowers while the new variety has red flowers. The female seed parent plant has red flowers with a diameter of 65 while the new variety has red flowers with a diameter of 45 mm.

The objective of the hybridization of this rose variety was to create a new and distinct variety with unique qualities, such as:

1. Uniform and abundant red flowers;
2. Vigorous, but compact growth when propagated on its own roots; and
3. Exceptional disease resistance.

This combination of qualities is not present in previously available commercial cultivars of this type, known to the inventor, and distinguish 'Poulty048' from all other varieties of which we are aware.

As part of the rose development program, Mogens N. Olesen germinated the seeds from the aforementioned hybridization during winter of 2019 and conducted evaluations on the resulting seedlings in a controlled environment in Fredensborg, Denmark. 'Poulty048' was selected in the spring of 2020 by the inventor as a single plant from the progeny of the aforementioned hybridization.

Asexual reproduction of 'Poulty048' by rooted cuttings was first done by Mogens N. Olesen in the nursery in Fredensborg, Denmark in July 2020. This initial and other subsequent asexual propagations conducted in controlled environments have demonstrated that the characteristics of 'Poulty048' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulty048'.

Specifically illustrated in FIG. 1 of the drawings are flowers at various stages of development viewed from the side, open flowers viewed from above, petals detached revealing reproductive flower parts and sepals detached revealing the receptacle.

Figure 1:
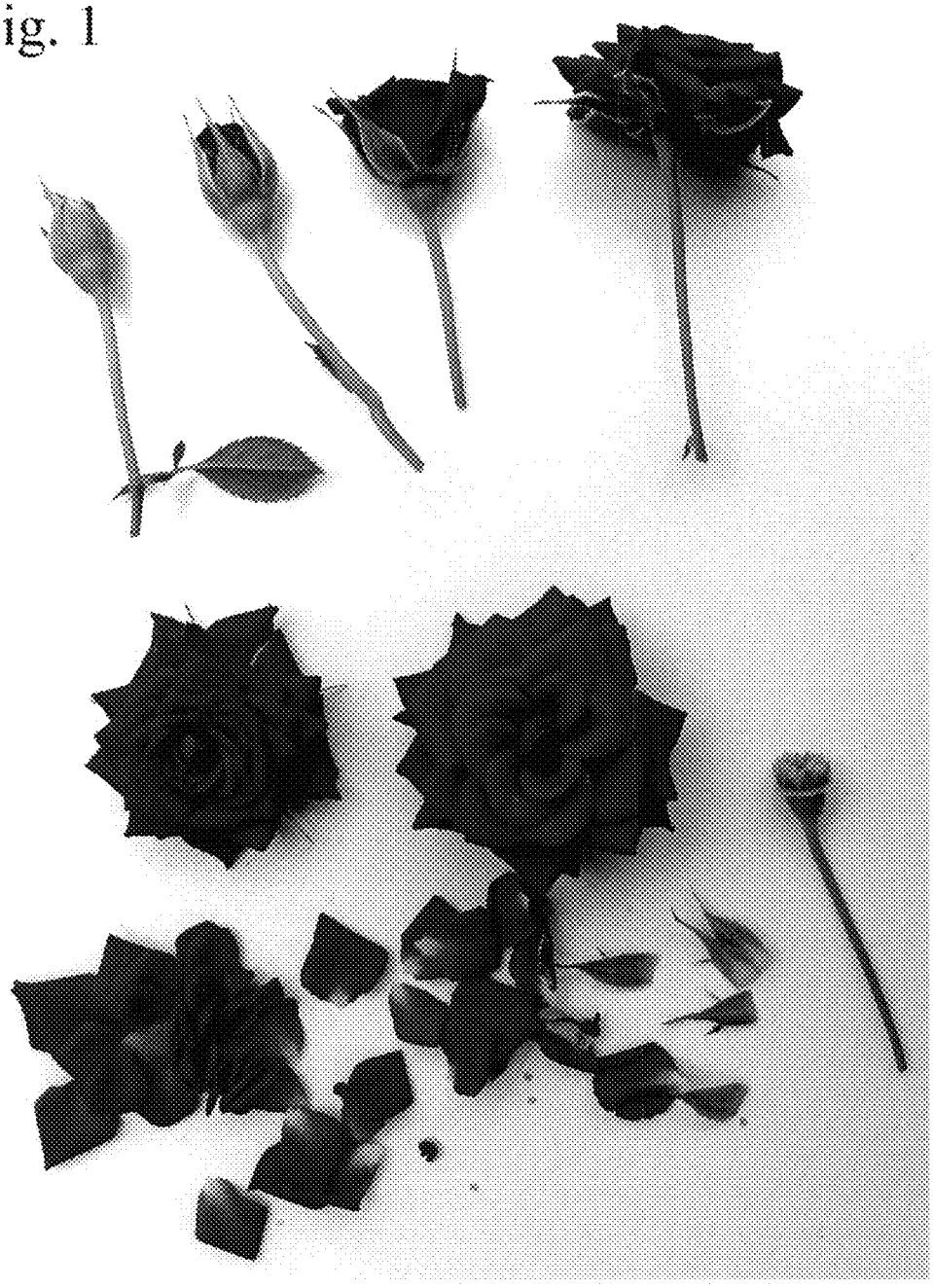
Figure 2:
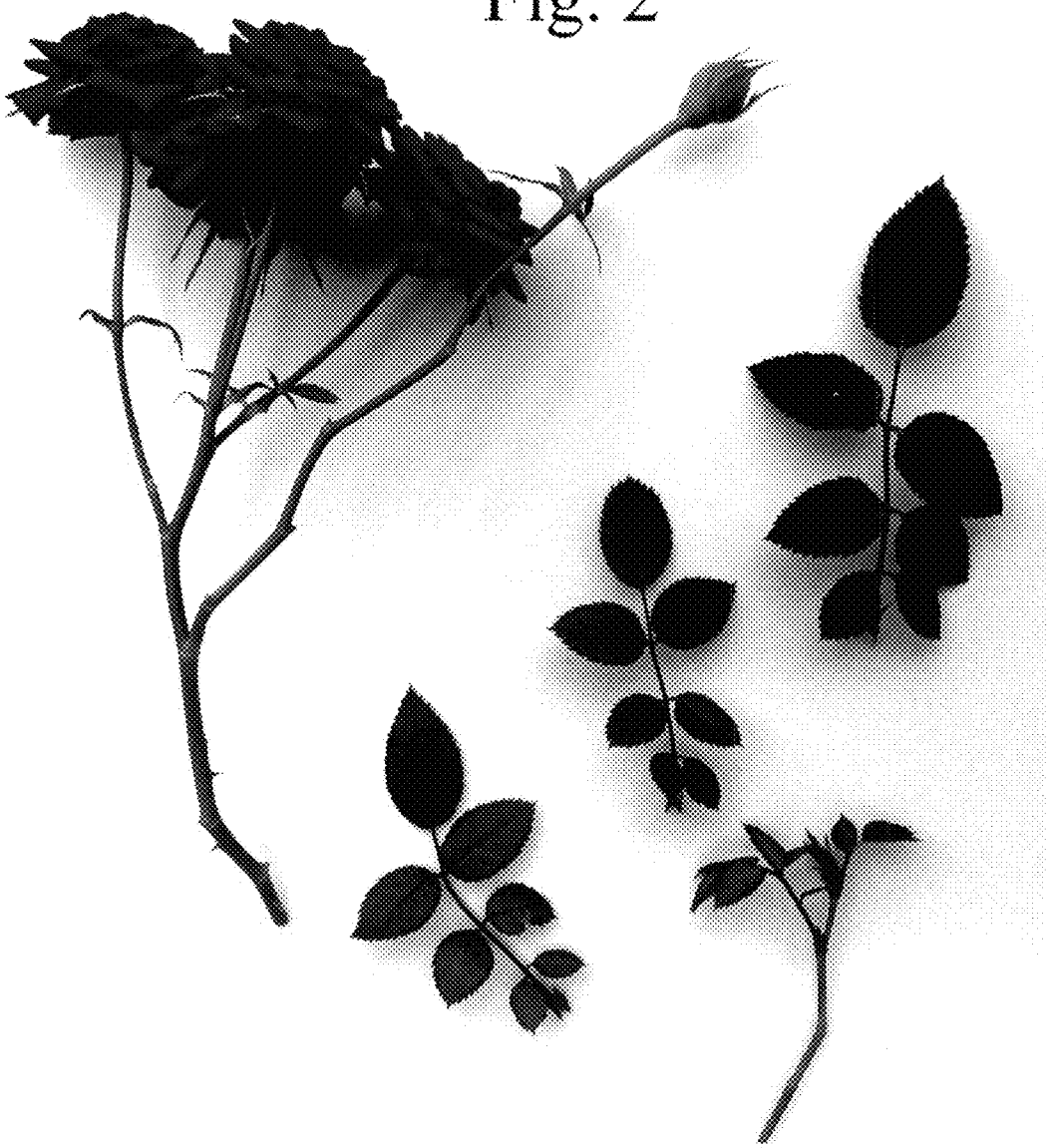

Specifically illustrated in FIG. 2 of the drawings is a cluster of flowers on a bare stem, juvenile growth, and mature leaves. Plants shown are 5 months of age.

DETAILED DESCRIPTION OF THE VARIETY

The following is a description of 'Poulty048', as observed in its growth in an indoor glasshouse nursery in Odense Denmark. Observed plants are 5 months of age, and were grown on their own roots in 23 cm pots. Color references are made using The Royal Horticultural Society (London, England) Colour Chart, 2001, except where common terms of color are used.

For a comparison, physical characteristics of the rose variety 'Poulpar029', U.S. Plant Pat. No. 16,148 are compared to the claimed plant. While 'Poulty048' has 50 flower petals, 'Poulpar029' has 30 flower petals. The claimed plant has a flower diameter of 45 mm while 'Poulpar029' has a flower diameter of 35 mm.

FLOWER AND FLOWER BUD

Blooming habit: Continuous.

Flower bud:

*Size.*—Upon opening, 22 mm in length from base of receptacle to end of bud. Bud diameter is 10 mm.

*Bud form.*—Urceolate.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Subulate. Apex: Caudate. Base: Flat at union with receptacle.

*Sepal margin.*—Margins have light foliaceous appendages on three of the five sepals.

*Sepal size.*—About 20 mm long, 6 mm wide.

*Receptacle.*—Texture: Smooth. Size: 5 mm in height, 6 mm wide. Color: Yellow-Green Group 144A. Shape: Campanulate.

*Pedicel.*—Surface: Smooth. Length: About 35 mm. Diameter: 2 mm on average. Color: Yellow-Green Group 144A. Strength: Strong.

*Peduncle.*—Length: 20 to 40 cm. Diameter: About 2 to 3 mm. Color: Yellow-Green Group 144B. Texture: Smooth.

Flower bud development: Flower buds are borne in clusters of 5 to 7 flower buds per stem.

Flower bloom:

*Fragrance.*—Light floral.

*Duration.*—The blooms have a duration on the plant of approximately 21 days. Petals fall cleanly away from plant after flowers have fully matured.

*Size.*—Flower diameter is 45 mm when open. Flower depth is 20 mm.

*Flower shape.*—Rosette, very double flower with many slightly overlapping petals of different sizes.

*Shape of flower, side view.*—The upper portion is convex. The lower portion is concave.

Petalage: Under normal conditions, flowers have about 50 petals.

General tonality of flower: Open flowers are Red Group 53A. After 10 days Red Group 53B.

Petal color:

*Upon opening, outer and inner petals.*—Upper surface: Red Group 53A with streaks of White Group N155A. Lower surface: Red-Purple Group 60A blended with Red Group 53A. Some outer guard petals have intonations of Yellow-Green Group 144A.

*Basal petal spots, upon opening.*—Upper surface: White Group N155A. Lower surface: White Group N155B.

*After opening, outer and inner petals.*—Upper surface: Red Group 53B. Lower surface: Red Group 53B with intonations of Red-Purple Group 60A.

*Basal petal spots, after opening.*—Upper surface: White Group N155A. Lower surface: White Group N155B.

Petals:

*Petal reflex.*—Strong, bilateral.

*Margin.*—Entire and uniform. Moderate undulations.

*Shape.*—Broad and elliptic. Apex shape: Rounded. Base shape: Acute.

*Size.*—Outer petals are 20 mm (l)×20 mm (w). Inner petals are 14 mm (l)×10 mm (w).

*Texture.*—Smooth on upper and lower surface.

*Thickness.*—Average.

Petaloids:

*Size.*—10 mm (l) by 8 mm (w).

*Quantity.*—About 5.

*Shape.*—Elliptical with an acute base and rounded apices.

*Color.*—The upper surface is Red Group 53A with streaks of White Group N155A. The lower surface is Red-Purple Group 60A blended with Red Group 53A.

Reproductive flower parts:

*Pollen.*—None observed.

*Anthers.*—Size: 1 mm in length. Color: Yellow Group 13A. Quantity: 65 on average.

*Filaments.*—Color: Yellow Orange Group 15D with intonations of Orange-Red Group 32C. Length: 3 mm.

*Pistils.*—Length: 4 mm. Quantity: 27 on average.

*Stigmas.*—Color: Yellow-White Group 158A.

*Styles.*—Color: Green-White Group 157A with intonations of Red Group 53C.

*Location of stigmas.*—Inferior in location relative to the length of the filaments and the height of the anthers.

*Hips.*—None Observed.

PLANT

Plant growth: Well branched, compact, and upright. Plants are 30 cm in height, and 50 cm wide.

Stems:

*Color of juvenile growth.*—Yellow-Green Group 144B.

*Color of mature growth.*—Yellow-Green Group 144A.

*Length.*—Canes are about 13 cm from the base of the plant to the flowering portion.

*Diameter.*—About 4 mm.

*Internodes.*—On mature canes about 17 mm between nodes.

*Surface texture.*—Young wood: Smooth. Older wood: Smooth.

Long prickles:

*Incidence.*—3 prickles per 10 cm of stem.

*Size.*'Average length of prickles on mature stems is 4 mm.

*Shape.*—Upper portion is linear. Lower portion is concave.

*Color.*—Juvenile prickles: Greyed-Red Group 182A. Mature prickles: Greyed-Red Group 182A.

Plant foliage:

*Compound leaf.*—About 100 mm (l)×60 (w).

*Quantity.*—4 leaves per 10 cm of stem on average.

*Leaf bearing angle to the stem.*—45 degrees.

*Color of juvenile foliage*.—Upper side: Yellow-Green Group 144A with intonations of Greyed-Purple Group 183B at margins. Lower side: Yellow-Green Group 144B shaded with Greyed-Purple Group 183B.

*Color of mature foliage*.—Upper side: Yellow-Green Group 147A. Lower side: Yellow-Green Group 146B.

Plant leaves and leaflets:

*Stipules*.—Size: 10 mm long, 4 mm wide. Quantity: 2 per compound leaf. Shape: Linear, slightly broad based with outward extending apices. Margins: Finely serrated. Color:

*Petiole*.—Length: 10 mm. Diameter: 1.5 mm. Upper surface color: Yellow-Green Group 144A with intonations of Greyed-Purple Group 185A. Lower surface color: Yellow-Green Group 144A. Texture: The lower and upper surfaces are smooth.

*Rachis*.—Length: 40 mm. Dimeter: 1.5 mm. Upper surface color: Greyed-Purple Group 185A. Lower surface color: Yellow-Green Group 144A. Texture: The lower surface is smooth with a few small flexible prickles. The upper surface is smooth somewhat glandular.

*Leaflet*.—Quantity: Normally 7 leaflets. Margins: Serrated. Size: Terminal leaflets are about 41 mm long, 23 mm wide. Shape: Generally elliptical. Base: Rounded. Apex: Acute. Texture: Smooth at the lower and upper surface. Thickness: Average. Arrangement: Odd pinnate. Venation: Reticulate. Glossiness: The upper surface is moderately glossy. The lower surface is not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

Pest resistance: The new variety is susceptible to ordinary pests that affect the species.

I claim:

1. A new and distinct variety of rose plant named 'Poulty048' substantially as described and illustrated herein.

* * * * *